United States Patent
Raza

(10) Patent No.: US 6,540,758 B1
(45) Date of Patent: Apr. 1, 2003

(54) APPARATUS FOR AND A METHOD OF PERFORMING ANASTOMOSIS OF BLOOD VESSELS

(76) Inventor: Syed Tasnim Raza, 1102 Admiral's Walk, Buffalo, NY (US) 14202

( * ) Notice: Subject to any disclaimer, the term of this patent is extended or adjusted under 35 U.S.C. 154(b) by 136 days.

(21) Appl. No.: 09/722,297

(22) Filed: Nov. 28, 2000

(51) Int. Cl.[7] ............................................... A61B 17/08
(52) U.S. Cl. ....................................... 606/153; 606/156
(58) Field of Search ................................ 606/153, 151, 606/152, 154, 155, 156, 99, 113; 623/1.11, 1.13, 2.11, 2.38

(56) References Cited

U.S. PATENT DOCUMENTS

| | | | |
|---|---|---|---|
| 4,202,479 A | 5/1980 | Razgulov et al. | |
| 4,553,543 A | 11/1985 | Amarasinghe | |
| 4,739,762 A | * 4/1988 | Palmaz ........................ | 128/343 |
| 4,930,674 A | 6/1990 | Barak | |
| 5,188,638 A | 2/1993 | Tzakis | |
| 5,222,963 A | * 6/1993 | Brinkerhoff et al. ......... | 606/153 |
| 5,254,127 A | 10/1993 | Wholey et al. | |
| 5,314,436 A | 5/1994 | Wilk | |
| 5,464,415 A | 11/1995 | Chen | |
| 5,503,638 A | 4/1996 | Cooper et al. | |
| 5,599,311 A | * 2/1997 | Raulerson .................... | 604/175 |
| 5,720,755 A | 2/1998 | Dakov | |
| 5,741,274 A | 4/1998 | Lenker et al. | |
| 5,814,057 A | 9/1998 | Oi et al. | |
| 5,947,363 A | 9/1999 | Bolduc et al. | |
| 6,030,392 A | 2/2000 | Dakov | |
| 6,050,472 A | * 4/2000 | Shibata ....................... | 227/175.2 |
| 6,053,390 A | * 4/2000 | Green et al. .............. | 227/179.1 |
| 6,241,762 B1 | * 6/2001 | Shanley ....................... | 623/1.17 |
| 6,248,117 B1 | * 6/2001 | Blatter ......................... | 606/153 |
| 6,413,274 B1 | * 7/2002 | Pedros ......................... | 623/2.11 |
| 6,443,958 B1 | * 9/2002 | Watson, Jr. et al. ......... | 606/120 |

* cited by examiner

Primary Examiner—John J. Calvert
Assistant Examiner—Alissa L. Hoey
(74) Attorney, Agent, or Firm—Diller, Ramik & Wight

(57) ABSTRACT

A tubular anvil sleeve is defined by at least two sleeve portions pivoted to each other for movement about an axis radially outwardly offset from an axis of the tubular anvil sleeve in its closed position. A tubular graft is inserted into the tubular anvil sleeve and a projecting end portion of the graft is folded over an exterior of the tubular annular sleeve. The tubular annular sleeve and the overfolded portion of the graft is inserted into an excised end of a blood vessel after which staples are ejected in a conventional manner. The tubular annular sleeve is removed by axial motion followed by relatively pivoting the sleeve portions about the pivot axis of the sleeve portions to open the tubular annular sleeve and effect the withdrawal/removal thereof.

13 Claims, 6 Drawing Sheets

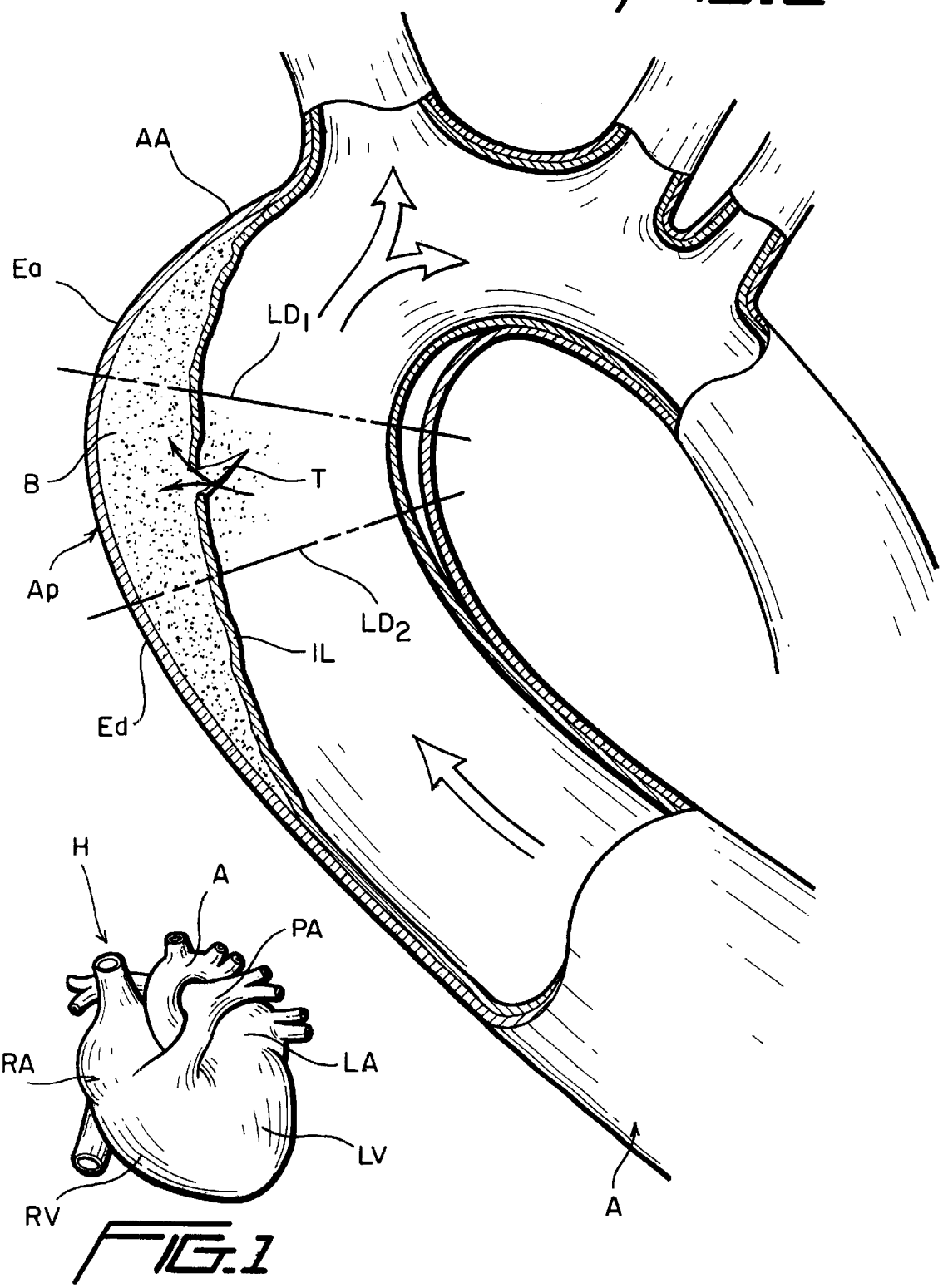

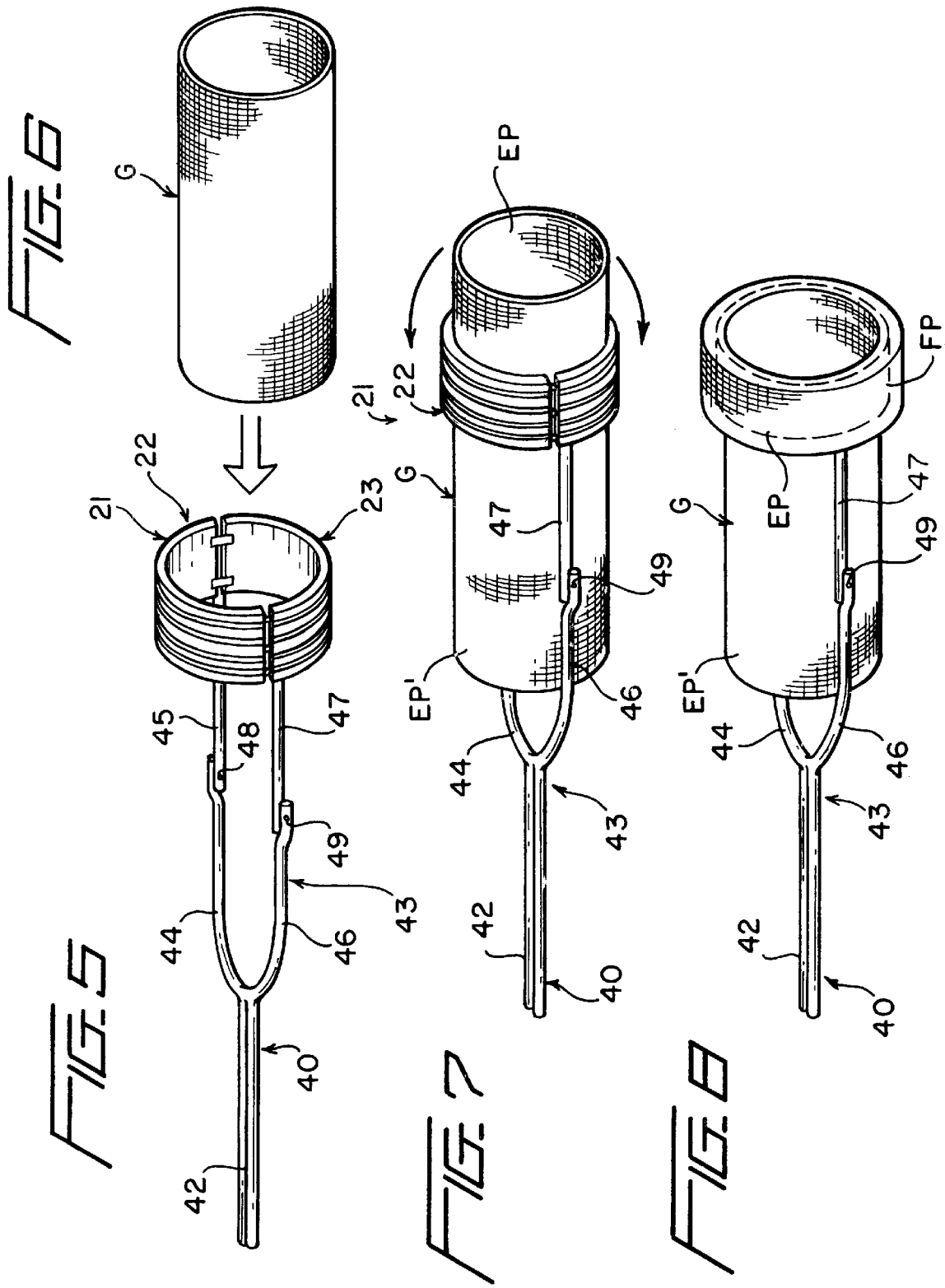

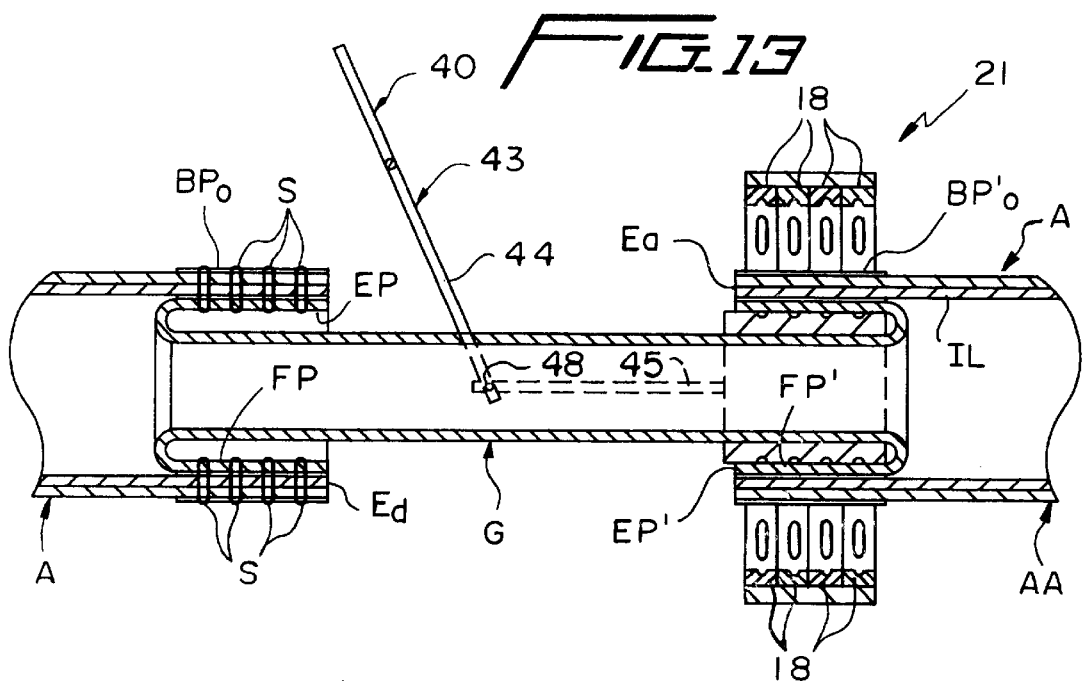
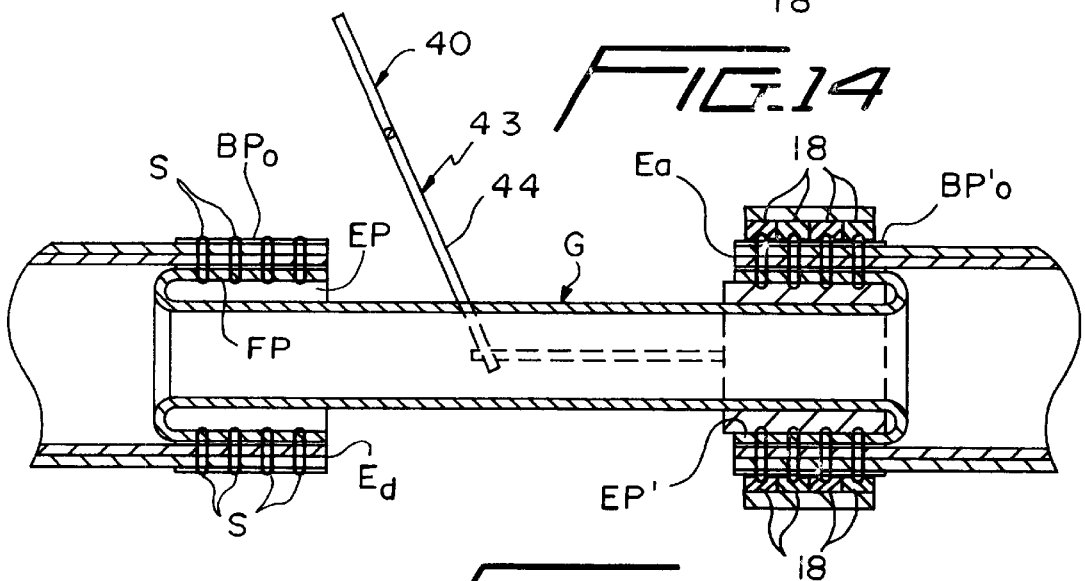
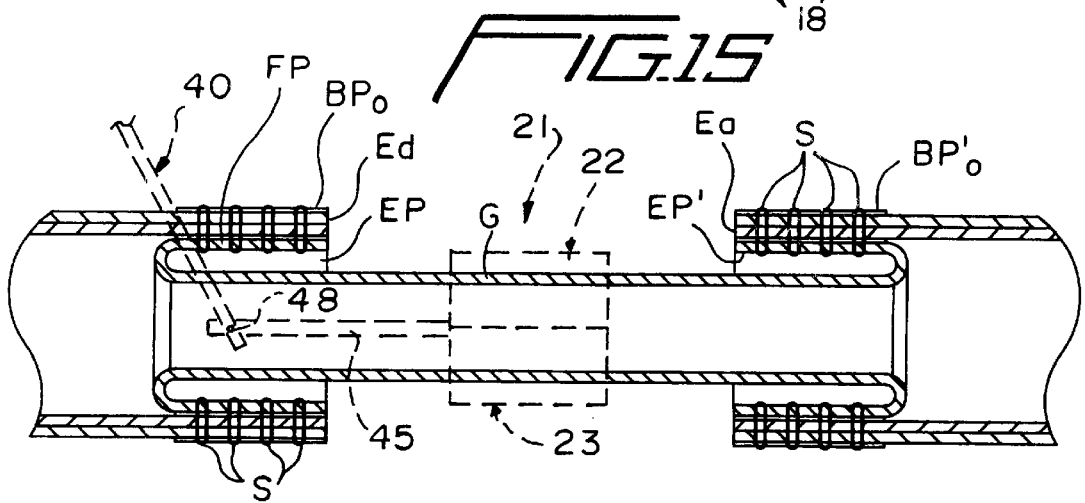

APPARATUS FOR AND A METHOD OF PERFORMING ANASTOMOSIS OF BLOOD VESSELS

FIELD OF THE INVENTION

The present invention pertains to the field of surgery and specifically to surgical suturing devices for and methods of aortic dissection including anastomosing a graft onto blood vessels, such as the aorta. However, the invention is equally applicable to joining any generally tubular vessels or organs to each other in end-to-end relationship.

One conventional way of connecting blood vessels is by the manual placement of sutures which is time consuming and demands highly specialized skills. It usually takes about ten to twenty minutes to complete each anastomosis. For many operative interventions, a number of such connections are required, and tissues which are deprived of blood supply during any particular procedure suffer from ischemia which can produce degenerative and necrotic changes. Bleeding also occurs frequently from such manually performed anastomoses which prolongs and complicates the procedures. Other disadvantages of manual suturing are apparent and more frequently automatic staplers are now used for suturing, particularly for suturing hollow organs in gastrointestinal surgery. U.S. Pat. No. 5,720,755 (Dakov) discloses a stapler which ejects staples axially relative to the walls of flanged or cuffed blood vessels, especially arteries, though such is said to be a difficult and time consuming procedure, as compared to that of gastrointestinal organs. One major difficulty involving cardiovascular surgery utilizing staples for suturing is the limited space within the operative area which makes conventional methods unsuitable for use with blood vessels. The latter patent makes reference to Pat. No. 5,188,638 (Tzakis) as an example of suturing vessel walls which must be cuffed in order to perform the procedure. A major disadvantage of the stapling device of the latter patent is the utilization of an annular anvil which is of an elliptical or ellipsoid configuration formed by two split halves which are lightly glued together. The annular anvil is not only difficult to position incident to the performance of the anastomosis procedure, but at the completion thereof the anvil must be essentially "broken" into two separate pieces to effect the removal of the two anvil parts from the cuffed organ or vessel which is also necessarily tied down to the annular anvil in and against an annular outwardly opening groove thereof, normally by conventional manually applied sutures. Thus, after the completion of the stapling operation, the sutures must also be removed and the annular anvil must thereafter be split and carefully removed which involves extremely delicate and facile efforts in a relatively small operative area.

BRIEF SUMMARY OF THE INVENTION

The present invention solves all of the aforementioned problems through the utilization of a novel suturing device, and particularly a novel tubular or annular anvil sleeve defined by at least two sleeve portions which are pivotally connected to each other for pivotal movement from a first closed tubular stapling position to a second open removal position. The pivoting motion is about a pivot axis which is substantially parallel to but radially outwardly offset from an axis defined by the tubular anvil sleeve in its closed position. Due to the latter construction, the anvil sleeve can be axially slid from an internal telescopic position relative to the stapled blood vessel and/or graft while closed and thereafter can be pivoted to its open position for removal. The suture, glueing and "breaking" of the tubular anvil of U.S. Pat. No. 5,188,638 is thus entirely eliminated along with the disadvantages associated therewith.

With the above and other objects in view that will hereinafter appear, the nature of the invention will be more clearly understood by reference to the following detailed description, the appended claims and the several views illustrated in the accompanying drawings.

BRIEF DESCRIPTION OF THE DRAWINGS

FIG. 1 is a perspective view of a human heart, and illustrates various portions thereof, including the aorta.

FIG. 2 is a highly enlarged perspective view of the aorta of FIG. 1 with portions broken away for clarity, and illustrates intimal and adventitial layers thereof, including an intimal tear in the intima or inner layer of the aorta.

FIG. 5 is a perspective view of the anvil, and illustrates the tubular anvil sleeve in its closed position incident to telescopically receiving therein a tubular Dacron® graft.

FIG. 6 is a perspective view of the Dacron® graft, and illustrates the same incident to being telescopically inserted into the tubular anvil sleeve of FIG. 5.

FIG. 7 is a perspective view, and illustrates the tubular graft telescopically inserted within the tubular anvil sleeve with an end portion of the tubular graft projecting to the right of the anvil sleeve, as viewed in FIG. 7.

FIG. 8 is a perspective view of the tubular anvil sleeve and the graft of FIG. 6, and illustrates the end portion of the tubular graft folded, overfolded or cuffed upon an exterior surface of the tubular anvil sleeve.

FIG. 13 is a generally axially view taken along line 13—13 of FIG. 11, and illustrates the externally reinforced ends of the ascending aorta, the stapler, the tubular anvil and the overfolded end of the tubular graft incident to closing the stapler and ejecting staples therefrom to complete the stapling.

FIG. 14 is a similar view taken along line 13—13 of FIG. 11, and illustrates the completion of the stapling operation.

FIG. 15 is a similar view take in along line 13—13 of FIG. 11, and illustrates the tubular anvil removed from the position of FIGS. 13 and 14 and the completed anastomosis of the aorta.

DETAILED DESCRIPTION OF THE PREFERRED EMBODIMENT

Figure 3:
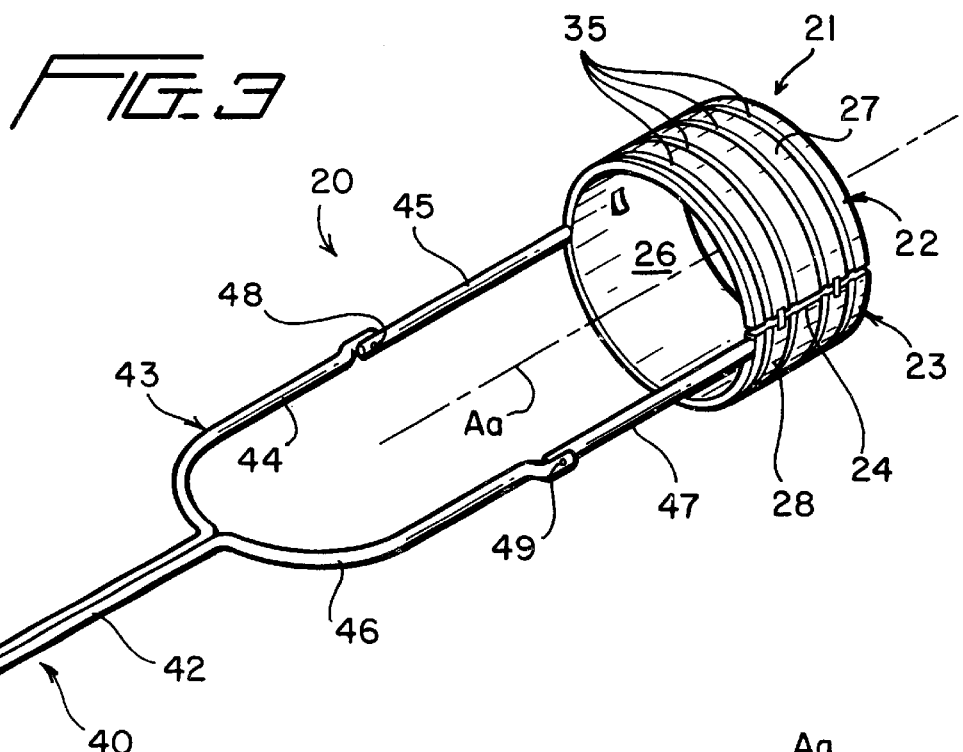
FIG. 3 is a perspective view of a novel anvil for use with a conventional stapler, and illustrates a tubular anvil sleeve in its closed position formed of two semi-circular anvil sleeve portions with the sleeve portions being pivotally connected to each other along a pivot axis radially offset from an axis of the tubular anvil sleeve when in its closed position, and a pivoted handle connected to one of the anvil sleeve portions.

A heart is illustrated in FIG. 1 of the drawings and is generally designated by the reference numeral H. The heart H includes a right atrium RA, a left atrium LA, a right ventricle RV, a left ventricle LV, a pulmonary artery PA, and an aorta A. The aorta A includes an intimal (inner) layer or intima IL (FIG. 2) and an adventitial (outer) layer or adventitia AL. In Type A or Type 1 aortic dissection the intimal (inner) layer or intima IL is torn and defines a tear T in the ascending aorta AA. Blood B collects in the volume (unnumbered) between the layers AL, IL which during surgery necessitates dissection of an aortic portion AP of the aorta A generally along lines of dissection LD1, LD2 thereby separating a distal end or end portion Ea of the ascending aorta AA from a proximal end or end portion Ed of the ascending aorta AA. The two ends or end portions Ea, Ed of the ascending aorta AA, after the dissected aorta portion AP and particularly the intimal portion thereof has been excised, are still quite fragile and the two layers AL, IL are still separated.

A surgical stapler 10 (FIG. 10) of the present invention is utilized both to reinforce each aortic end Ea, Ed with a bovine pericardium layer BPo on the outside which are held together with three or four circumferential rows R (FIG. 9) of staples S. The reinforcing bovine pericardium layer BPo makes it easier for anastomosing a graft G (FIGS. 6 through 15) of Dacron® or equivalent material.

The surgical stapler 10 (FIGS. 10 and 11) includes a conventional stapling device 11 corresponding to the anastomotic surgical fastener driving instrument of U.S. Pat. No. 5,188,638 and a novel anvil 20 of the present invention.

The stapling device 11 includes a pair of handles 13, 14 pivotally connected together by a pivot 15 and carrying respective annular stapling jaw halves 16, 17, each having one or more rows of cartridges 18 which eject the conventional staples S radially inwardly in a conventional manner which will be described more fully hereinafter.

Figure 4:
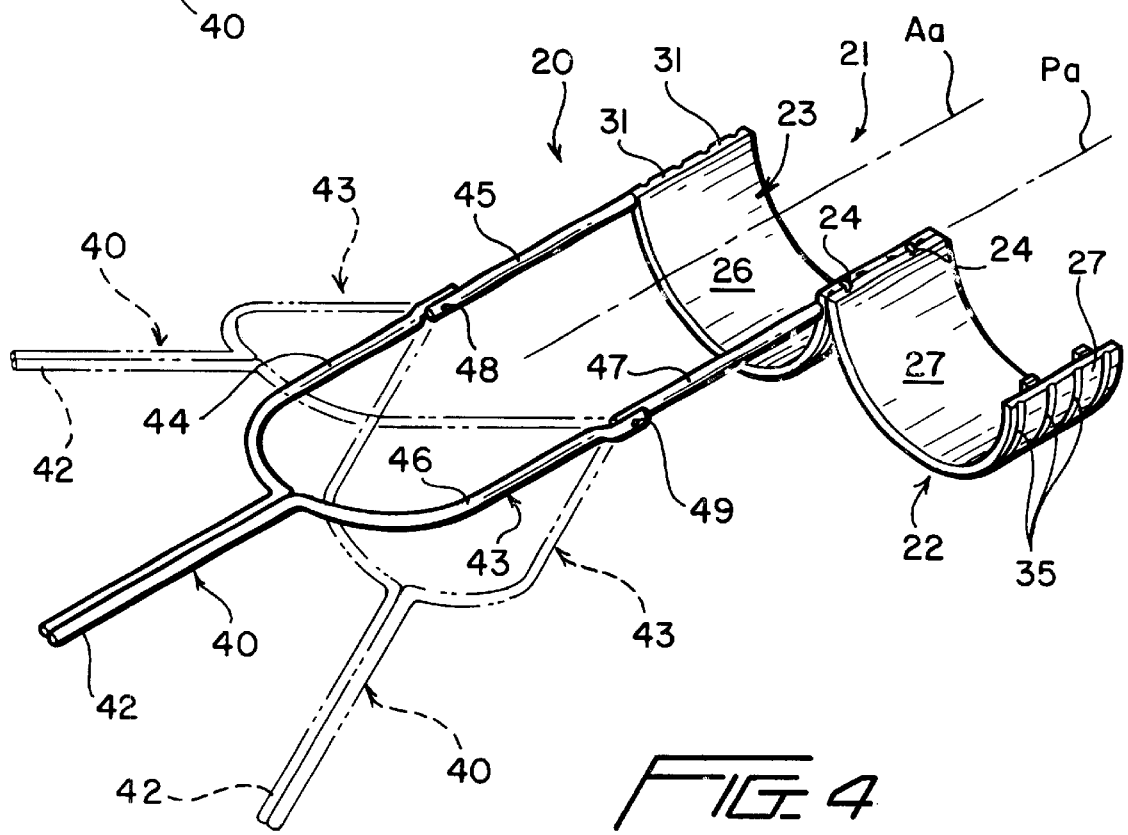
FIG. 4 is a perspective view of the anvil or tubular anvil sleeve of FIG. 3, and illustrates the tubular anvil sleeve in its open position, and a portion of the pivoted handle shown in phantom outline illustrating two of many positions of use of the handle.

The anvil 20 (FIGS. 3 through 8 of the drawings) includes a substantially tubular anvil sleeve 21 defined by at least two sleeve portions 22, 23, each of a generally semi-cylindrical configuration which are pivotally connected to each other by a pivot means 24 in the form of a conventional pivot. The sleeve portions 22, 23 include respective inner surfaces 25, 26 and outer surfaces 27, 28, the latter two of which define a generally continuous exterior cylindrical surface 27, 28 in the closed position (FIG. 3) of the tubular anvil sleeve 21. Conventional latching means 30 in the form of projecting male latching tongues 30 are carried by the sleeve portion 22 and are releasably snap-secured into female latch-receiving openings 31 of the sleeve portion 23. The male latching tongues 30 securely snap secure in the female openings 31 to retain the tubular anvil sleeve in its closed position (FIG. 3) during the stapling operation, yet permit the snap release thereof in a conventional manner to effect pivoting of the sleeve portions 22, 23 relative to each other about the pivot 24 from the stapling position (FIG. 3) to the applying/removing position (FIG. 4). The relative pivoting of the sleeve portions 23, 24 takes place about a pivot axis Pa (FIG. 4) which is radially outwardly offset from an axis Aa of the tubular anvil sleeve defined when in the closed position thereof (FIG. 3).

The exterior surfaces 27, 28 include a plurality of shallow outwardly opening cylindrical grooves 35 with four such grooves being illustrated and corresponding in location to the four cartridges 18 (FIG. 13) and the staples S associated therewith.

A handle 40 is defined by a generally Y-shaped anvil portion 41 which includes a gripping portion 42 and a bight portion 43 having a first leg 44,45 pivoted together at 48 and a second leg 46, 47 pivoted together at 49 with the legs 45, 46 being welded or otherwise fastened to the sleeve portion 23. The pivots 48, 49 permit the manipulation of the anvil 20 when used in aortic dissection and anastomosis, as will be described immediately hereinafter.

Aortic Anastomosis

Figure 9:
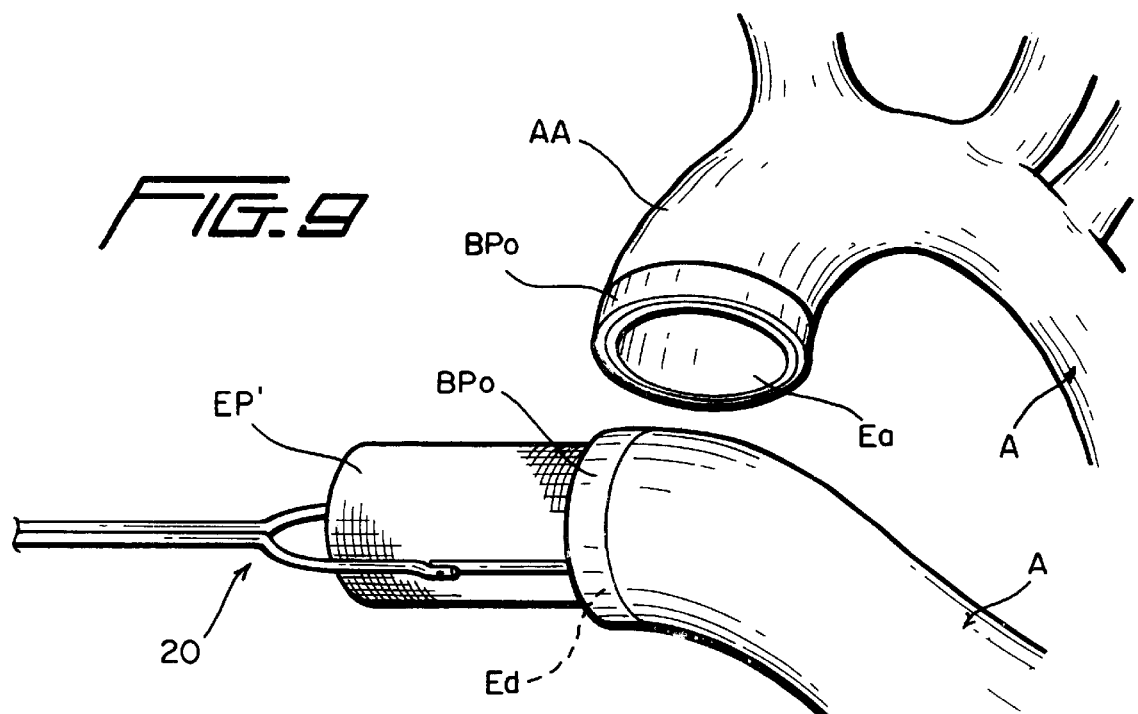
FIG. 9 is a perspective view, and illustrates the anvil with the overfolded graft end portion inserted within an externally reinforced end of the proximal end of the ascending aorta after the intimal torn portion of the aorta had been excised.
Figure 10:
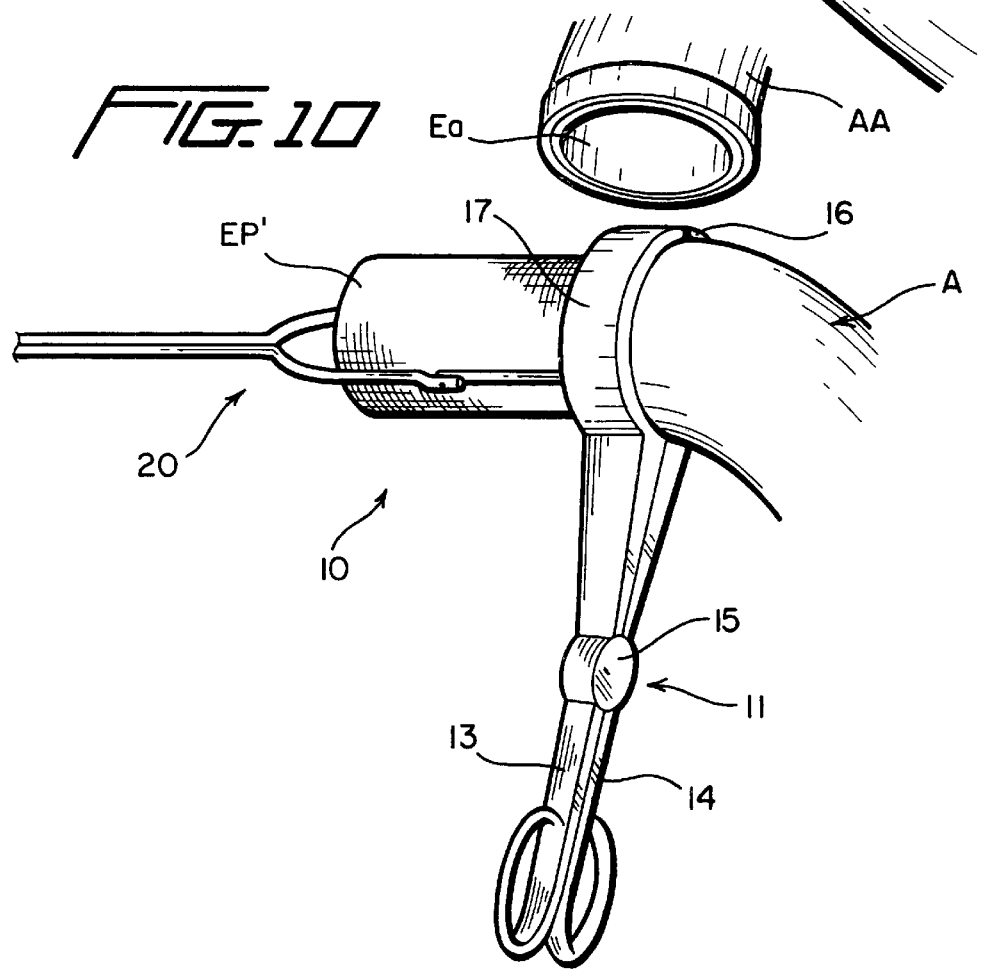
FIG. 10 is a perspective view similar to FIG. 9, and illustrates a conventional stapler in external surrounding relationship to the tubular anvil sleeve incident to ejecting staples radially inwardly to suture the tubular graft to the externally reinforced proximal end of the ascending aorta.
Figure 11:
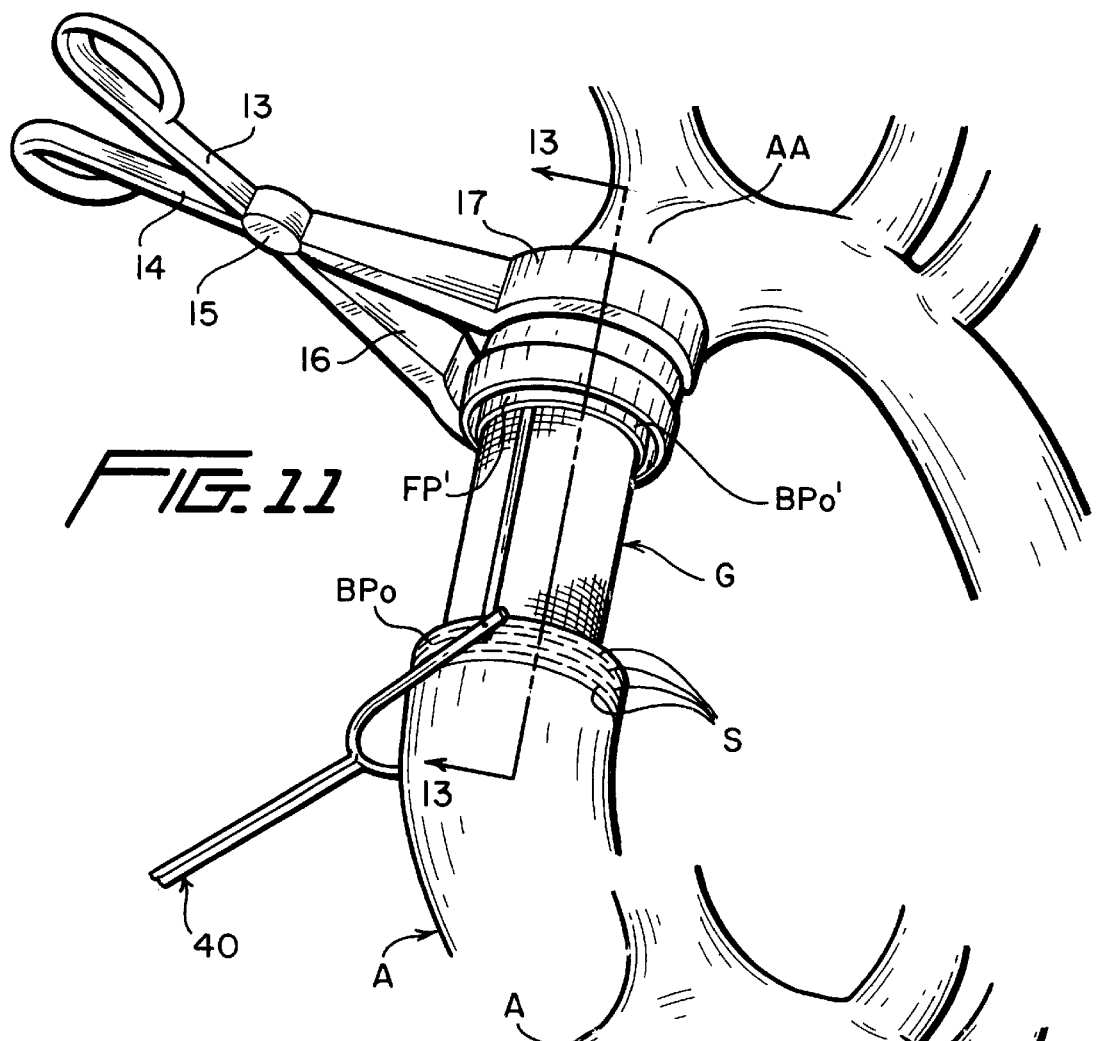
FIG. 11 is a perspective view similar to FIG. 10, and illustrates the tubular anvil sleeve and the stapler removed from the relationship shown in FIG. 10 with respect to the proximal end of the ascending aorta and repositioned relative to the distal end of the ascending aorta incident to stapling the reinforced end of the distal end of the ascending aorta to an opposite overfolded portion of the graft.
Figure 12:
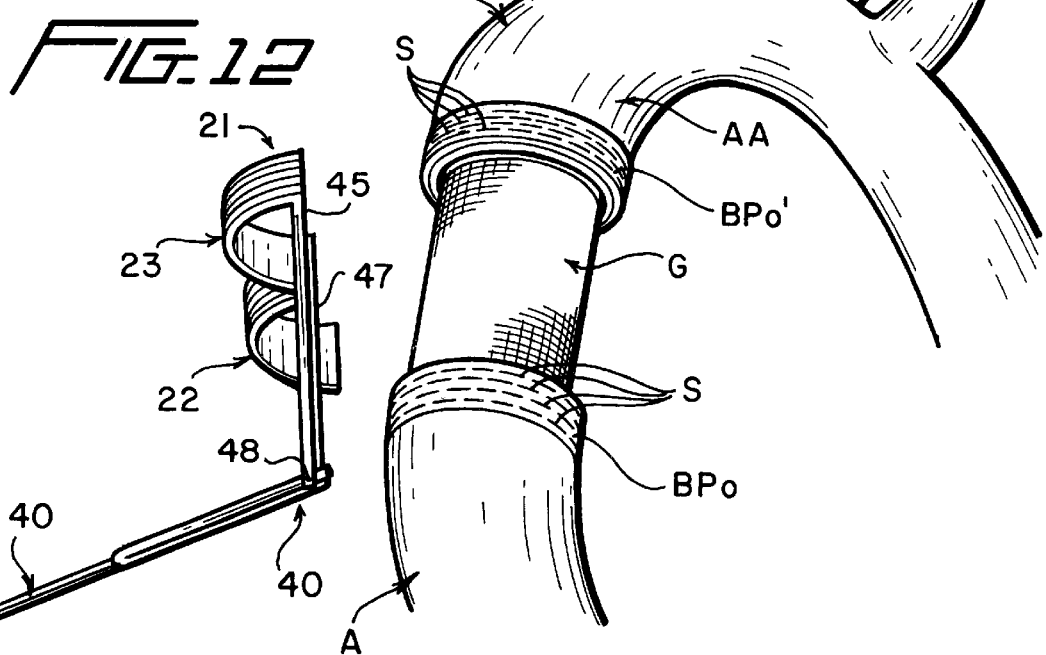
FIG. 12 is a perspective view illustrating the removal of the tubular anvil sleeve, and illustrates the same after being drawn axially downwardly from the position shown in FIG. 11 to a position (not shown) surrounding only the tubular graft after which the tubular annular sleeve is pivoted, fully opened and radially withdrawn to the illustrated position.

After the aortic portion AP (FIG. 2) has been dissected, the Dacron® graft G (FIG. 6) is axially inserted into the closed tubular anvil sleeve 21 in the manner graphically depicted in FIGS. 5 through 7 of the drawings. Alternately, the Dacron® graft G can be seated upon or between either of the sleeve portions 22, 23 when in the open position thereof (FIG. 4) after which the sleeve portions 22 and 23 are closed to the position shown in FIG. 7. An end portion EP of the Dacron® graft G projects axially beyond (to the right, as viewed in FIG. 7) the anvil sleeve 21 and is thereafter reverse folded or folded over and generally upon the exterior cylindrical surfaces 27, 28 of the closed tubular anvil sleeve 21 in the manner illustrated in FIG. 8 with the folded portion of the Dacron® graft G being designated by the reference character FP. The folded portion FP is then inserted into either the distal end Ea of the ascending aorta AA or the proximal end Ed of the ascending aorta AA, and in FIG. 9 the folded portion FP is shown inserted into the proximal end Ed of the ascending aorta AA sufficiently for receipt therein of the tubular anvil sleeve 21. Thus, the folded portion FP of the graft G and the anvil sleeve 21 are inserted inside the intima IL which is enveloped or telescoped over the same and also within the adventitial AL after which an outer reinforcing layer of bovine pericardium PBo is positioned in surrounding relationship to the exterior of the adventitial AP and in surrounding relationship to the underlying folded portion FP of the Dacron® graft G. Thereafter, the stapling device 11 is manipulated from an open position to the closed position shown in FIG. 10 in which the stapler jaw halves 16, 17 telescopically exteriorly embrace the reinforcing bovine pericardium outer layer PBo, the underlying portions of the adventitia AP and intima AL and the overfolded portion FP of the Dacron® graft G after which the staples S are fired resulting in the anastomosis shown at the left side of FIG. 13 after the anvil has been removed by simply sliding the anvil sleeve 21 to the left, as viewed in FIGS. 9 and 10, beyond the Dacron® graft G. At this stage of the anastomosis, the tubular anvil sleeve 21 need not be opened to remove the same after the performance of the stapling operation because the left hand end of the graft G, again as viewed in FIGS. 9 and 10, is free and the closed anvil sleeve 21 can be slid to the left and freely removed therefrom.

The distal end Ea of the ascending aorta AA is next anatomized by positioning an end portion EP' of the Dacron graft G opposite the end portion EP thereof in overfolded or folded relationship to the closed tubular anvil sleeve 21 in the manner illustrated in FIG. 13 of the drawings. The end portion EP' can be telescoped into the closed tubular anvil sleeve 21 or positioned within the opened sleeve portions 22, 23 thereof (FIG. 4) after which the latter are closed and the end portion EP' is then folded to the position shown in FIG. 13, just as was earlier described with respect to the end portion EP. The handle H is appropriately manipulated during this procedure, including during the insertion of the tubular anvil sleeve 21 and the end portion EP' of the graft G into the distal end Ea of the ascending aorta AA, in the manner illustrated in the right hand side of FIG. 13. Once again, an outer reinforcing layer of bovine pericardium BP'o is positioned in surrounding relationship to the exterior of the adventitia AL (FIG. 13), the stapler jaw halves 16, 17 are positioned as shown in FIG. 13, eventually closed (FIG. 14) and the staples S are ejected from the cartridges 18 in a conventional manner resulting in the completion of the anastomosis of the aorta A, except, of course, for the removal of the closed tubular anvil sleeve 21 from the position shown in FIG. 14.

Referring specifically to FIG. 14, the anvil 20 and specifically the tubular anvil sleeve 21 is removed from the anatomized aorta A and the external surrounding relationship of the sleeve 21 to the Dacron® graft G by first sliding the closed tubular annular sleeve 21 to the left from the position shown in FIG. 14 to the position shown in FIG. 15 by appropriately manipulating and pulling the handle 40 until the closed anvil sleeve 21 is positioned generally as illustrated in FIG. 15. Thereafter, the latching means 30, 31 are unlatched, the sleeve portions 22, 23 are opened, and the anvil 20 can be readily removed from the anatomized aorta A.

Although a preferred embodiment of the invention has been specifically illustrated and described herein, it is to be understood that minor variations may be made in the apparatus without departing from the spirit and scope of the invention, as defined the appended claims.

What is claimed is:

1. An anvil for use with a stapler operative for stapling end portions of tubes to each other comprising a substantially tubular anvil sleeve having an exterior surface, said exterior surface including means against which staples are driven and closed, said tubular anvil sleeve including at least two sleeve portions, and means for pivotally connecting said sleeve portions for pivotal movement from a first closed tubular stapling position to a second open removal position by relative pivoting movement about a pivot axis substantially parallel to and radially outwardly offset from an axis defined by said sleeve in said closed position whereby subsequent to the performance of a stapling operation said anvil sleeve can be removed from exterior surrounding relationship to a stapled end portion of a tube by pivoting said sleeve portions about said pivotally connecting means from said first closed tubular stapling position to said second open position.

2. The anvil as defined in claim 1 including a handle connected to one of said sleeve portions.

3. The anvil as defined in claim 1 including a handle connected to only one of said sleeve portions.

4. The anvil as defined in claim 1 including a handle, and means for pivotally connecting said handle to one of said sleeve portions.

5. The anvil as defined in claim 1 including a handle, and means for pivotally connecting said handle to only one of said sleeve portions.

6. The anvil as defined in claim 1 including a handle, and means for pivotally connecting said handle to only one of said sleeve portions for pivoting movement about an axis substantially transverse to said first-mentioned pivot axis.

7. The anvil as defined in claim 1 including a handle, and means for pivotally connecting said handle to only one of said sleeve portions for pivoting movement about an axis substantially transverse to said first-mentioned pivot axis.

8. The anvil as defined in claim 1 including a handle, and means for pivotally connecting said handle to only one of said sleeve portions for pivoting movement ab out an axis substantially normal to said first-mentioned pivot axis.

9. The anvil as defined in claim 1 including a handle, and means for pivotally connecting said handle to only one of said sleeve portions for pivoting movement about an axis substantially normal to said first-mentioned pivot axis.

10. The anvil as defined in claim 1 wherein said exterior surface includes means for closing staples adapted to be fired from a stapling head.

11. The anvil as defined in claim 1 wherein said exterior surface includes groove means for closing staples adapted to be fired from a stapling head.

12. The anvil as defined in claim 1 wherein said exterior surface includes a plurality of axially spaced circumferential groove means for closing staples adapted to be fired from a stapling head.

13. The anvil as defined in claim 1 wherein said exterior surface includes a plurality of axially spaced endless circumferential groove means for closing staples adapted to be fired from a stapling head.

* * * * *